(12) United States Patent
Peng et al.

(10) Patent No.: US 9,243,044 B2
(45) Date of Patent: Jan. 26, 2016

(54) ANTICOAGULANT POLYPEPTIDE AND APPLICATIONS THEREOF

(75) Inventors: Lifei Peng, Zhanjiang (CN); Weiqiong Gan, Zhanjiang (CN); Zheng Shao, Zhanjiang (CN); Qingfeng He, Zhanjiang (CN); Li Deng, Zhanjiang (CN); Jingjing Hu, Zhanjiang (CN); Shuli Liao, Zhanjiang (CN); Jida Peng, Zhanjiang (CN)

(73) Assignee: GUANGDONG MEDICAL COLLEGE, Zhanjiang, Guangdong (CN)

( * ) Notice: Subject to any disclaimer, the term of this patent is extended or adjusted under 35 U.S.C. 154(b) by 0 days.

(21) Appl. No.: 14/111,470

(22) PCT Filed: Apr. 5, 2012

(86) PCT No.: PCT/CN2012/073509
§ 371 (c)(1),
(2), (4) Date: Oct. 21, 2013

(87) PCT Pub. No.: WO2012/116663
PCT Pub. Date: Sep. 7, 2012

(65) Prior Publication Data
US 2014/0323404 A1    Oct. 30, 2014

(30) Foreign Application Priority Data
Apr. 15, 2011 (CN) .......................... 2011 1 0097205

(51) Int. Cl.
*A61K 38/00* (2006.01)
*C07K 14/435* (2006.01)

(52) U.S. Cl.
CPC ............. *C07K 14/4354* (2013.01); *A61K 38/00* (2013.01)

(58) Field of Classification Search
CPC ............. A61K 38/00; C07K 14/43504; C07K 14/4354
USPC ........................................ 514/13.7; 530/324
See application file for complete search history.

(56) References Cited

FOREIGN PATENT DOCUMENTS

| AU | 2012100391 A4 | 5/2012 |
| CN | 101260150 A | 9/2008 |
| CN | 102241734 A | 11/2011 |

OTHER PUBLICATIONS

Water from www.biology-online-org/dictionry/Water, pp. 1-3. Accessed Apr. 24, 2014.*
ABP88128 from NCBI. Accessed Jan. 14, 2015.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Deng et al., "Identification of an anticoagulant peptide that inhibits both fXIa and fVIIa/tissue factor from the blood-feeding nematode *Ancylostoma caninum*", Biochemical and Biophysical Research Communications, vol. 392, 2010, pp. 155-159.
International Search Report for PCT/CN2012/073509 mailed on Jun. 28, 2012.

* cited by examiner

*Primary Examiner* — Julie Ha
(74) *Attorney, Agent, or Firm* — Birch, Stewart, Kolasch & Birch, LLP

(57) ABSTRACT

Disclosed is an anticoagulant polypeptide and applications thereof. The anticoagulant polypeptide comprises a polypeptide formed by an amino acid sequence as represented in Seq. ID No. 1; or comprises a derived polypeptide that selectively inhibits coagulation factor XIa and is formed by an amino acid sequence, as represented in Seq. ID No. 1, that has undergone one or multiple amino acid residue substitutions, deletions, or insertions. The anticoagulant polypeptide is a selective inhibitor for coagulation factor XIa, has anticoagulant activity and small side-effect, and can be used in preparing medicines for the prevention and treatment of thrombotic diseases.

12 Claims, 1 Drawing Sheet

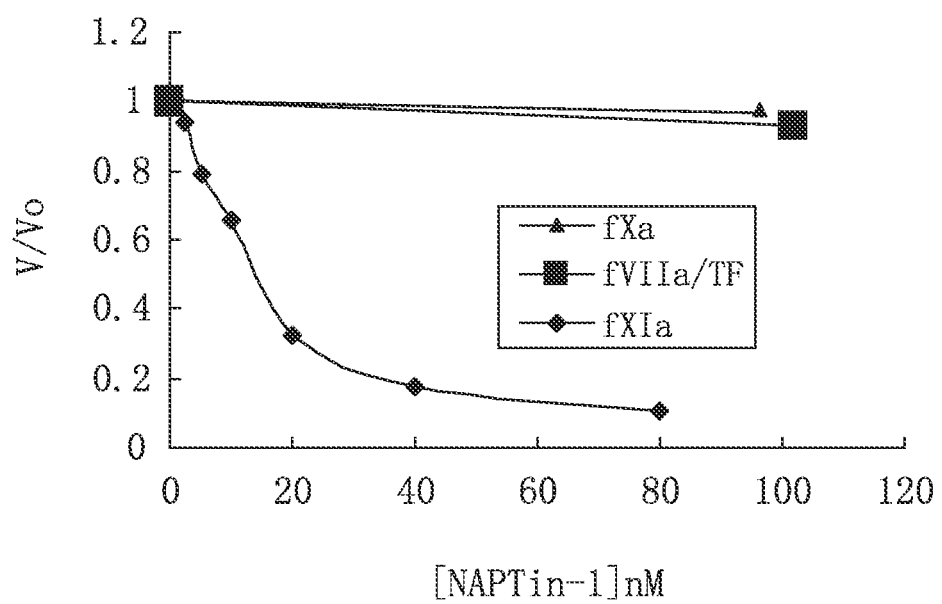

ANTICOAGULANT POLYPEPTIDE AND APPLICATIONS THEREOF

FIELD OF THE INVENTION

The present invention belongs to the field of biomedicine. Specifically, the present invention relates to an anticoagulant polypeptide and its applications in the preparation of drugs for the prevention and treatment of thromboembolic diseases.

BACKGROUND OF THE INVENTION

Thromboembolic diseases, especially the cardiovascular and cerebrovascular thromboembolic diseases, are common disease that seriously threaten the health of the population and cause high fatality and disability rate. Currently available anticoagulants, such as heparin (includes low molecular weight heparin (LMWH) such as enoxaparin), warfarin, platelet aggregation inhibitors (such as aspirin) and hirudin are already approved for clinical use, however, these anticoagulants increase the bleeding risk in patient. Bleeding is one of the most common and serious complications in the clinical anticoagulant and antithrombotic therapies, thus it is very important to develop novel anticoagulant and antithrombotic drugs with lower bleeding risk. The clinical data and a series of animal experimental studies indicate that fXIa (or fXI) should be a novel target for the protection against thrombosis with lower bleeding risk in recent years. So develop drugs target fXIa (or fXI) may be an alternative way to treat and prevent thromboembolic diseases with lower bleeding risk.

High level of factor XI is a risk factor for deep venous thrombosis (Meijers J C M et al. N Engl J Med. 2000; 342: 696-701), and fXI-deficient patients reduce the incidence of deep vein thrombosis and ischemic stroke (Salomon O et al. Thromb Haemost. 2011, 105:269-73; Salomon O et al. Blood. 2008, 111: 4113-4117). These data suggest that the deficiency or inhibition of fXI/fXIa are associated with protection against thrombosis. Moreover, human deficiency in FXI results in a rare bleeding disorder and show seldom spontaneous bleeding (Seligsohn U. J Thromb Haemost. 2009, 7 (suppl): 84-87). It suggests that the deficiency or inhibition of fXI/fXIa has minimal or no bleeding risk in human.

In animal models, the fXI knockout mice do not have excessive bleeding when challenged by surgical procedures, and they have normal hemostatic capacity but have significantly reduced venous and arterial thrombosis in response to various mechanical and chemical vessel injuries. FXI antibody effectively reduced thrombosis in the rats, rabbits and baboons, and had little effect on the bleeding time (Renné T et al. J Thromb Haemost. 2009, Suppl 1: 79-83). The fXI monoclonal antibody (aXIMab) reduced thrombus formation and thrombin generation in the baboon's artificial vessels, but had little or no effect on the bleeding time and platelet aggregation activity, therefore, blocking the fXI may offer therapeutic advantages over other antithrombotic agents in terms of bleeding complications (Tucker et al. Blood. 2009, 113: 936-944). Comparing with enoxaparin and warfarin, the antisense oligonucleotides (ASOs) for fXI effectively reduced venous thrombosis and arterial thrombosis without causing bleeding; ASOs increased the antithrombotic activity of the enoxaparin and clopidogrel but did not increase bleeding (Zhang H et al. Blood. 2010, 116 (22): 4684-4692), and was considered as a safer anticoagulant.

It's confirmed that the mice knocked out of tissue factor (TF), fVII, fV, fX and prothrombin can't live for a long time (Mackman N. Arterioscler Thromb Vasc Biol. 2005, 25: 2273-228), while fVIII$^{-/-}$ and fIX$^{-/-}$ deficient mice can survive, but show bleeding diathesis, which similar to the human hemophilia that caused by the deficiency of fVIII or fIX. However, fXI knockout mice (fXI$^{-/-}$ mice) can live healthy with normal hemostatic function. Moreover, The fXI knockout mice are protected from thrombus formation when compared to wild-type animals (Gailani D, Renné T. J Thromb Haemost 2007, 5: 1106-1112).

As mentioned above, the fXI deficiency and inhibition have been shown to be associated with lower bleeding risk. It means that the drugs target fXIa or fXI has advantages of lower bleeding risk compares with that target thrombin, fX, fVII, and other coagulation factors. At present, only a few candidates including fXI antibody, fXI antisense oligonucleotides, peptidomimetics, some small chemical molecules and a molecule in a sponge (Schumacher W A et al. Arterioscler Thromb Vasc Biol. 2010, 30 (3): 388-392) target fXIa have been found, while selective peptide inhibitor target fXIa still keep to be not found.

Hookworms are blood-feeding intestinal nematodes that can cause chronic gastrointestinal blood loss of their hosts. They secrete antihemostatic molecules to counteract host hemostatic responses and result in bleeding. We recently isolated a novel anticoagulant peptide, named AcaNAP10 from the hookworm *Ancylostoma caninum*, which can inhibit both fXIa and fVIIa/TF. Significantly, AcaNAP10 was the first anticoagulant that inhibits both fXIa and fVIIa/TF (Li D, et al. Biochem Biophys Res Commun. 2010, 392 (2):155-9).

In order to obtain specific inhibitors of fXIa, based on the amino acid sequence of AcaNAP10, we invented a series of anticoagulant polypeptides that can selectively inhibit fXIa. These anticoagulant polypeptides can be used for development of novel anticoagulant drugs to treat or prevent thromboembolic disease with lower bleeding risk.

SUMMARY OF THE INVENTION

The purpose of the present invention is to provide an anticoagulant polypeptide and applications thereof. The polypeptide is a selective inhibitor of fXIa with significantly prolonging the plasma activated partial thromboplastin time (aPTT) but little effect on the prothrombin time (PT). So it can be used for development of novel anticoagulant drugs to treat or prevent thromboembolic disease with lower bleeding risk.

The anticoagulant polypeptide provided in the present invention includes the polypeptide comprised of the amino acid sequence shown in SEQ ID NO.1, or derivative polypeptide derived from SEQ ID NO.1 by substitution, deletion or insertion of one or several amino acids, which can selectively inhibit coagulation factor XIa.

The anticoagulant polypeptide provided in the present invention includes the polypeptide comprised of the amino acid sequence shown in SEQ ID NO.2, or SEQ ID. NO.3, or SEQ ID. NO.4, or SEQ ID NO.5, or SEQ ID NO.6, or SEQ ID NO.7, or SEQ ID, NO.8, or SEQ ID NO.9 or SEQ ID NO.10.

AcaNAP10 can inhibit both fXIa and fVIIa/TF, however, anticoagulant polypeptide provided in the present invention are selective inhibitors which have potent inhibitory activity against fXIa, but almost have no inhibition of fVIIa/TF. In addition, they can significantly prolong the aPTT, while have little effect on the PT.

The anticoagulant polypeptide provided in the present invention have antithrombotic activity, but little or no effect on hemostasis, platelet aggregation activity. So these anticoagulant polypeptides in the present invention can be used for the development of novel anticoagulants to treat and prevent thromboembolic disease with little side effect.

After the disclosing of the present invention, the applications of these anticoagulant polypeptides can be easily understood and implemented. For example, the anticoagulation polypeptide provided in the present invention in combination with other anticoagulant agents, antithrombotic drugs can reduce bleeding risk. Anticoagulant polypeptide provided in the present invention can be produced by genetic engineering or chemical synthesis. The anticoagulant polypeptide provided in the present invention can be as compositions in anticoagulant preparations can be used in clinical.

The advantage of the anticoagulant polypeptide provided in the present invention is that they are selective inhibitors of fXIa, The anticoagulant polypeptide provided in the present invention can be used as drugs for the preventment and treatment of thromboembolic diseases with lower bleeding risk. It will be of a great value for the reduction of bleeding complications in the clinical anticoagulant and antithrombotic therapies.

DESCRIPTION OF THE DRAWING

The following drawing is only for the purpose of description and explanation but without being limited to these, FIG. 1 shows the inhibition of NAPTin-1 against fXIa, fXa and fVIIa/TF.

DESCRIPTION OF PREFERRED EMBODIMENT

The present invention is illustrated by the following examples. It should be understood that the embodiments of the present invention is only for the purpose of illustration but without being limited to these. Any equivalent replacement in accordance with the present invention will following into the scope of the invention.

Example 1

Preparation of the Anticoagulant Polypeptide to Selectively Inhibit fXIa

The series of primers were designed according to the sequence encoding AcaNAP10 (Li D et al. Biochem Biophys Res Commun. 2010, 392:155-159). By using these primers, the deletion mutants were amplified by PCR and each mutant was sequentially shortened one amino acid from the C-terminal of AcaNAP10. The results showed that the AcaNAP10 mutants, from NAPTin-1 to NAPTin-10, have selective inhibition on fXIa but no or weak inhibition on fVIIa/TF. The amino acid sequence of NAPTin-1 is shown in SEQ ID NO: 1, the amino acid sequence of NAPTin-2 is shown in SEQ ID NO: 2, the amino acid sequence of NAPTin-3 is shown in SEQ ID NO: 3, the amino acid sequence of NAPTin-4 is shown in SEQ ID NO: 4, the amino acid sequence of NAPTin-5 is shown in SEQ ID NO: 5, the amino acid sequence of NAPTin-6 is shown in SEQ ID NO: 6, the amino acid sequence of NAPTin-7 is shown in SEQ ID NO: 7, the amino acid sequence of NAPTin-8 is shown in SEQ ID NO: 8, the amino acid sequence of NAPTin-9 is shown in SEQ ID NO: 9, the amino acid sequence of NAPTin-10 is shown in SEQ ID NO: 10, respectively.

Example 2

Anticoagulant Activity of the Anticoagulant Polypeptide

The recombinant anticoagulant polypeptides were expressed in *Escherichia coli* and purified in our laboratory. Anticoagulant activity was determined by measuring the aPTT and PT.

For the PT assay, 10 µl recombinant protein at various concentration was mixed with 45 µl normal human plasma and incubated for 15 mins at 37° C. 45 µl prewarmed PT reagent (MDC Hemostasis, Germany) was then added and the clotting time was measured with the absorbance at 630 nm by using an E1x808 kinetic microtiter reader (BioTek, United States). Each concentration was repeated 3 times.

For the aPTT assay, 10 µl recombinant protein at various concentrations was mixed with 50 µl fresh normal human plasma, 20 µl aPTT reagent (MDC Hemostasis, Germany) and incubated for 15 mins at 37° C. 20 µl 0.05 mol/L prewarmed $CaCl_2$ was then added to initiate the clotting reaction. The clotting time was measured with the absorbance at 630 nm by using an E1x808 kinetic microtiter reader (BioTek, United States). Each concentration was repeated 3 times. The ratio of the mean aPTT value of each concentration to blank control group is multiples of prolonging the aPTT.

As shown in Table 1, at concentrations of 100 nM and 500 nM, NAPTin-1, NAPTin-2, NAPTin-3, NAPTin-4, NAPTin-5, NAPTin-6, NAPTin-7, NAPTin-8 and NAPTin-9 could significantly prolong aPTT, respectively, but NAPTin-1, NAPTin-2, NAPTin-3, NAPTin-4, NAPTin-5, NAPTin-6 and NAPTin-7 couldn't prolong PT. Meanwhile, NAPTin-8 and NAPTin-9 almost couldn't prolong PT at the concentrations of 100 nM, but they could prolong less than 1.6 times PT at the concentrations of 500 nM.

TABLE 1

Effect of the anticoagulant polypeptides on aPTT and PT

| NAP | Concentration nM | aPTT and multiples of prolonging aPTT | | PT (sec) |
|---|---|---|---|---|
| | | aPTT (sec) | multiples of prolonging aPTT | |
| NS | | 40.1 ± 4.2 | | 12.5 ± 0.8 |
| NAPTin-1 | 100 | 79.2 ± 3.5* | 1.98 | 12.4 ± 0.9 |
| | 500 | 228.3 ± 7.4* | 5.69 | 12.1 ± 0.4 |
| NAPTin-2 | 100 | 80.2 ± 5.1* | 2.0 | 11.7 ± 1.1 |
| | 500 | 221.8 ± 6.3* | 5.53 | 12.6 ± 0.5 |
| NAPTin-3 | 100 | 83.0 ± 1.2* | 2.07 | 13.5 ± 0.4 |
| | 500 | 219.3 ± 6.2* | 5.47 | 12.3 ± 0.8 |
| NAPTin-4 | 100 | 78.7 ± 3.7* | 1.96 | 12.4 ± 0.9 |
| | 500 | 233.3 ± 4.5* | 5.82 | 11.6 ± 0.3 |
| NAPTin-5 | 100 | 77.9 ± 2.9* | 1.94 | 12.2 ± 0.6 |
| | 500 | 226.8 ± 6.6* | 5.66 | 12.6 ± 0.4 |
| NAPTin-6 | 100 | 79.5 ± 3.1* | 1.98 | 12.4 ± 0.9 |
| | 500 | 215.4 ± 5.6* | 5.37 | 12.6 ± 0.4 |
| NAPTin-7 | 100 | 78.7 ± 8.1* | 1.96 | 11.7 ± 0.5 |
| | 500 | 218.3 ± 5.9* | 5.44 | 12.7 ± 0.4 |
| NAPTin-8 | 100 | 79.7 ± 2.9* | 1.99 | 12.8 ± 0.7 |
| | 500 | 238.6 ± 8.1* | 5.95 | 17.6 ± 0.6# |
| NAPTin-9 | 100 | 80.8 ± 3.2* | 2.01 | 13.0 ± 0.7 |
| | 500 | 235.3 ± 5.4* | 5.87 | 19.6 ± 0.9# |

Comparison with saline group,
*p < 0.01;
Comparison with saline group,
p < 0.01

Example 3

Inhibitory Activity of the Anticoagulant Polypeptide Against Coagulation Factor

The recombinant anticoagulant polypeptides in the present invention were expressed in *E. coli* and purified in our laboratory, of which the activities against coagulation factors were investigated by chromogenic assays. Human coagulation factors IIa (thrombin), Xa, XIa, XIIa, EGR-fXa were products of Haematologic Technologies Inc (United States). Recombinant fVIIa was products of Novo-Nordisk (Denmark). Recombinant soluble tissue factor (sTF) was purchased from Protgen (Beijing, China). The following chromogenic substrates were used for these coagulation factor assays: S2765 for human fXa, S2288 for human fVIIa and fIIa, 52366 for human fXIa and fXIIa, respectively.

The chromogenic assays were carried out in a total reaction volume of 100 μl in individual wells of a 96-well microtiter plate. 50 μl fIIa, fXa, fXIa, or fXIIa (final concentration: 1 nM) was incubated with 10 μl recombinant anticoagulant polypeptide at various concentrations (or PBS control group) Assays for the detection activity of fVIIa: 50 μl fVIIa+TF (1 μM) and EGR-fXa (final concentration 500 nM) was incubated for 15 mins at 25° C., respectively. After the addition of 40 μl of prewarmed chromogenic substrate to a final concentration of 400 μM, the changes of absorbance at 405 nm were monitored by using an E1x808 kinetic microtiter reader. The data were used to calculate the velocities of response. The ratios of velocities in the presence and the absence of the recombinant anticoagulant polypeptide showed the relative inhibition to coagulation factor.

It is indicated that at the concentration of 100 nM, NAPTin-1, NAPTin-2, NAPTin-3, NAPTin-4, NAPTin-5, NAPTin-6, NAPTin-7, NAPTin-8 and NAPTin-9 inhibited more than 90% of the activity of fXIa without affecting fIIa, fXa, fXIIa and fVIIa/TF activities. At the concentration of 200 nM, NAPTin-1, NAPTin-2, NAPTin-3, NAPTin-4, NAPTin-5, NAPTin-6 and NAPTin-7 almost completely inhibited the activity of fXIa without affecting fIIa, fXa, fXIIa and fVIIa/TF activities. However, the recombinant anticoagulant polypeptide at the concentration of 200 nM had no significant inhibitory activity against fVIIa/TF except NAPTin-8 and NAPTin-9 inhibited about 15% of the activity of fVIIa/TF.

These results indicate that the anticoagulant polypeptides in the present invention are selective inhibitors of fXIa.

The inhibitory activity of various concentration of NAPTin-1 against fXIa, fXa and fVIIa/TF is shown in FIG. 1, V0 represents the velocities of substrate hydrolysis in the absence of NAPTin-1, V represents in the presence of NAPTin-1, V/V0 is the ratios that show inhibitory activity of NAPTin against coagulation factor. The activity of fXIa is gradually suppressed by increasing the concentration of NAPTin-1. NAPTin-1 inhibited fXIa with IC50 values of 18.7 nM. And NAPTin-1 at the concentration of 100 nM has no significant inhibitory activity against fVIIa/TF and fXa.

Example 4

Effect of the Anticoagulant Polypeptide on Mouse Tail Bleeding Time

130 SPF BALb/c mice (provided by the laboratory animal center of Guangdong Medical College, half male and half female, 19-23 g body weight) were randomly divided into saline group, and recombinant NAPTin-1, NAPTin-3, NAPTin-5, NAPTin-7 group The low dose (100 μg·kg$^{-1}$), middle dose (1.0 mg·kg$^{-1}$), and high dose (5.0 mg·kg$^{-1}$) of recombinant anticoagulant peptide was injected into the mouse tail veins, respectively. After 10 min, the distal tip 1.5 mm of the mouse tail was transected and the blood oozed was soaked with filter paper very 30 seconds until the bleeding stops. The bleeding time was defined as the time elapsed from the tail transection to the stoppage of bleeding. The results are shown in Table 2

TABLE 2

Effect of recombinant NAPTin-1, NAPTin-3, NAPTin-5 and NAPTin-7 on mouse tail bleeding time

| Group (dose) | Quantity (n) | Bleeding time (min) |
|---|---|---|
| saline group | 10 | 8.31 ± 2.4 |
| NAPTin-1 low dose group (100 μg · kg$^{-1}$) | 10 | 8.34 ± 1.7 |
| NAPTin-1 middle dose group (1 mg · kg$^{-1}$) | 10 | 8.30 ± 2.1 |
| NAPTin-1 high dose group (5 mg · kg$^{-1}$) | 10 | 8.28 ± 2.3 |
| NAPTin-3 low dose group (100 μg · kg$^{-1}$) | 10 | 8.38 ± 1.3 |
| NAPTin-3 middle dose group (1 mg · kg$^{-1}$) | 10 | 8.29 ± 2.5 |
| NAPTin-3 high dose group (5 mg · kg$^{-1}$) | 10 | 8.32 ± 1.8 |
| NAPTin-5 low dose group (100 μg · kg$^{-1}$) | 10 | 8.30 ± 2.3 |
| NAPTin-5 middle dose group (1 mg · kg$^{-1}$) | 10 | 8.31 ± 1.0 |
| NAPTin-5 high dose group (5 mg · kg$^{-1}$) | 10 | 8.33 ± 2.4 |
| NAPTin-7 low dose group (100 μg · kg$^{-1}$) | 10 | 8.30 ± 2.0 |
| NAPTin-7 middle dose group (1 mg · kg$^{-1}$) | 10 | 8.26 ± 1.9 |
| NAPTin-7 high dose group (5 mg · kg$^{-1}$) | 10 | 8.31 ± 2.2 |

Compared with saline group, the anticoagulant polypeptide groups had no significant effect on the bleeding time, which indicates the anticoagulant polypeptides of in the present invention have no significant effect on normal hemostatic function in mice. Thus, the anticoagulant peptides of in the present invention can be used to develop novel anticoagulant agents with lower bleeding risk.

Example 5

Effect of Recombinant NAPTin-1 (rNAPT-1) on Thrombus Formation in Rat Arterio-Venous Shunt Model 50 SPF grade male SD rats (provided by the laboratory animal center of Guangdong Medical College, 300-350 g body weight) were randomly divided into saline control group, positive control group (100 U·kg$^{-1}$ heparin sodium, Shanghai No. 1 Biochemical & Pharmaceutical Co. Ltd), and rNAPT-1 low dose (100 μg·kg$^{-1}$), middle dose (1 mg·kg$^{-1}$), high dose group (5 mg·kg$^{-1}$), 10 rats each group, respectively. These rats were anaesthetized with 10% chloral hydrate (250 mg/kg) by intraperitoneal injection. The right common carotid artery and left external jugular vein was exposed and dissected bluntly from the surrounding tissue after a surgical incision. One end of a polyethylene pipe (1.5 mm of diameter, 22 cm of length) with a 5 cm length of No. 4 operation suture in it and filled with 50 U/mL heparin solution was inserted into the right common carotid artery, and the other end was inserted into the left external carotid vein. 5 min after tail intravenous injection of drugs, the artery clamp was opened, and blood flow from the right common carotid artery to the left external jugular vein through the polyethylene pipe. After 15 min of blood flow, the suture line was quickly removed and weighed. The net weight of thrombus is total weight minus suture weight; inhibition rate=(wet weight of thrombus of saline control group−wet weight of thrombus of administration group)/wet weight of thrombus of saline control group× 100%. Compared with saline control group, the recombinant anticoagulant peptide NAPTin-1 could inhibit rat arteriovenous shunt thrombosis (P<0.01). The results are shown in Table 3.

TABLE 3

Effect of rNAPTin-1 on the arterio-venous thrombosis model in rats

| Groups (dose) | animal number (n) | wet weight of thrombus (mg) | Inhibition rate % |
|---|---|---|---|
| The saline control group | 10 | 55.1 ± 10.2 | |
| Heparin sodium (100 U · kg$^{-1}$) | 10 | 14.2 ± 3.6* | 74.3 |
| Low dose NAPTin-1 group (100 μg · kg$^{-1}$) | 10 | 8.5 ± 1.8* | 80.5 |
| Middle dose NAPTin-1 group (1 mg · kg$^{-1}$) | 10 | 1.5 ± 0.3* | 97 |
| High dose NAPTin-1 group (5 mg · kg$^{-1}$) | 10 | 0.3 ± 0.2* | 99 |

Compared with saline control group,
*p < 0.01

Example 6

Effect of rNAPT-1 on Rat Carotid Artery Thrombosis

50 SPF grade male SD rats (provided by the laboratory animal center of Guangdong Medical College, 300-350 g body weight) were randomly divided into sham operation group (except without the FeCl$_3$, the remaining steps with other groups), model group, and rNAPTin-1 low dose (100 μg·kg$^{-1}$), middle dose (1 mg·kg$^{-1}$), high dose group (5 mg·kg$^{-1}$), 10 rats each group, respectively. These rats were anaesthetized with 10% chloral hydrate (250 mg/kg) by intraperitoneal injection. The right carotid artery was isolated by making a midline cervical incision followed by blunt dissection to expose a 1 cm segment of the vessel from the carotid sheath, and then a 0.6 cm wide sealing adhesive strip was inserted. After 5 mins of tail intravenous injection of drugs, separation spare the common carotid artery segment was ring wrapped by filter paper (1.0 cm×0.5 cm) soaked in 20% FeCl$_3$ solution and sealed with strip seal. After 15 mins, the filter strips was remove. 40 mins later, the blood vessels ligation at both ends of filter paper was ligated. The vascular segment of the paper strip wrapped was precisely cut followed sucked excess blood in blood vessels with a clean filter paper, and wet weight including thrombotic vascular was accurately weighed, then weighed again after removing blood clots. The difference is the quality of the thrombus within the 0.5 cm long vessel segment. In sham operation, FeCl$_3$ immersion filter strips were replaced with normal saline immersion filter strips. Results are shown in Table 4.

TABLE 4

Effect of rNAPTin-1 on rat carotid artery thrombosis

| Groups (dose) | animal number (n) | wet weight of thrombus (mg) | Inhibition rate % |
|---|---|---|---|
| Sham operation group | 10 | 0 | |
| The model group | 10 | 4.5 ± 1.0 | |
| Low dose NAPTin-1 group (100 μg · kg$^{-1}$) | 10 | 1.5 ± 0.2* | 66.7 |
| Middle dose NAPTin-1 group (1 mg · kg$^{-1}$) | 10 | 0.5 ± 0.3* | 88.9 |
| High dose NAPTin-1 group (5 mg · kg$^{-1}$) | 10 | 0* | 100 |

Compared with the model group,
*p < 0.01

Example 7

Effect of rNAPTin-1 on Rat Venous Thrombosis

40 SPF grade male SD rats (provided by the laboratory animal center of Guangdong Medical College, 300-350 g body weight) were randomly divided into saline group, and rNAPTin-1 low-dose (100 μg·kg$^{-1}$), middle-dose (1 mg·kg$^{-1}$), high dose group (5 mg·kg$^{-1}$), 10 rats each group, respectively. These rats were anaesthetized with 10% chloral hydrate (250 mg/kg) by intraperitoneal injection. The inferior vena cava was exposed and dissected bluntly from the surrounding tissue after an abdominal surgical incision, After 5 min of tail intravenous injection of rNAPTin-1, Venous thrombosis was induced by tight ligation of the inferior vena cava just below the left renal venous using a thread. then the abdominal cavity was closed provisionally. The abdominal cavity was reopened after 4 hours, and the ligated segment was opened longitudinally to check for whether there is thrombus. The ratio of thrombus formation in rats was shown in Table 5. This result suggests that NAPTin-1 has a significant antithrombotic effect on rat venous thrombosis.

TABLE 5

Effect of rNAPTin-1 on rat inferior vena cava thrombosis

| | | | Thrombosis | |
|---|---|---|---|---|
| Group | Quantity (n) | Dose (mg/kg) | rate | Inhibition Rate (%) |
| saline Group | 10 | / | 10/10 | / |
| NAPTin-1 high dose group | 10 | 5.0 | 0/10* | 100% |
| NAPTin-1 middle dose group | 10 | 1.0 | 0/10* | 100% |
| NAPTin-1 low dose group | 10 | 0.1 | 2/10* | 80% |

Compared with saline Group,
*p < 0.01

Example 8

The Effect of rNAPTin-1 on the Clotting Time

40 SPF grade male SD rats (provided by the laboratory animal center of Guangdong Medical College, 300-350 g body weight) were randomly divided into a line group, and rNAPTin-1 low-dose (100 μg·kg$^{-1}$), middle-dose (1 mg·kg$^{-1}$), high dose group (5 mg·kg$^{-1}$), 10 rats each group. 2 min after intravenous injection of various rNAPTin-1, blood was harvested from animal heart, and injected into an anticoagulant tube (3.8% sodium citrate). Animal plasma was separated by centrifugation (1500×g, 10 mins) and was used to measure aPTT and PT. As shown in Table 6, rNAPTin-1 prolonged significantly aPTT, but not prolonged PT.

TABLE 6

The effect of rNAPTin-1 on rat clotting time

| | | | Clotting time | |
|---|---|---|---|---|
| Group | Quantity (n) | Dose (mg/kg) | aPTT | PT |
| saline Group | 10 | / | 16.2 ± 2.7 | 11.7 ± 0.7 |
| NAPTin-1 high dose group | 10 | 5.0 | 136.7 ± 35.5* | 11.5 ± 0.8 |
| NAPTin-1 Medium dose group | 10 | 1.0 | 56.3 ± 5.1* | 12.0 ± 0.3 |

TABLE 6-continued

The effect of rNAPTin-1 on rat clotting time

| Group | Quantity (n) | Dose (mg/kg) | Clotting time aPTT | PT |
|---|---|---|---|---|
| NAPTin-1 low dose group | 10 | 0.1 | 23.5 ± 2.1* | 11.8 ± 0.5 |

Compared with saline Group,
*p < 0.01

Whilst the above has been given by way of illustrative examples of the present invention, many variations and modifications thereto will be apparent to those skilled in the art without departing from the broad ambit and scope of the invention as herein set forth in the following claims.

INDUSTRIAL APPLICABILITY

The anticoagulant polypeptide provided in the present invention is that they are selective inhibitors of fXIa. The anticoagulant polypeptide provided in the present invention is not only can be used as drugs to prevent and treat thromboembolic diseases, but also has little or no effect on human or animal hemostasis, which meaning lower bleeding risk, so it will be of a great value for the reduction of bleeding complications in the clinical anticoagulant and antithrombotic therapies.

The invention claimed is:

1. An anticoagulant polypeptide for pharmaceutical application comprising:
a mutant polypeptide of *A. canium* nematode anticoagulant peptide 10 (AcaNAP10) having C-terminal amino acids deleted and having up to 76 amino acids, wherein the mutant polypeptide comprises SEQ ID NO: 7 and has selective inhibition on factor XIa (fXIa), but no or weak inhibition on factor VIIa-tissue factor complex (fVIIa/TF).

2. The anticoagulant polypeptide of claim 1, wherein the inhibition is determined in a chromogenic assay in a total reaction volume of 100 µl having 1 nM human coagulation factor IIa (fIIa), factor Xa (fXa), factor XIa (fXIa), or factor XIIa (fXIIa), or 1 nM factor VIIa (fVIIa)+1 µM soluble tissue factor (sTF)+500 nM active site-blocked factor Xa containing Glu-Gly-Arg chloromethyl (EGR-fXa),
incubating with 10 µl of recombinant anticoagulant polypeptide at a concentration of 100 nM, wherein the incubating is for 15 minutes at 25° C.,
adding of 40 µl of prewarmed chromogenic substrate to a final concentration of 400 µM, wherein the chromogenic substrate is S2765, S2288, and/or S2366,
measuring the changes of absorbance at 405 nm using a microtiter reader, and
obtaining response velocities in presence or absence of the recombinant anticoagulant polypeptide,
wherein the inhibition is a ratio of the response velocities of 90% or more with fXIa and without fIIa, fXa, fXIIa, and/or fVIIa/TF.

3. The anticoagulant polypeptide of claim 2, wherein the mutant polypeptide is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 8, SEQ ID NO: 9, and SEQ ID NO: 10.

4. The anticoagulant polypeptide of claim 2, wherein the mutant polypeptide is SEQ ID NO: 1.

5. The anticoagulant polypeptide of claim 2, wherein the mutant polypeptide is SEQ ID NO: 2.

6. The anticoagulant polypeptide of claim 2, wherein the mutant polypeptide is SEQ ID NO: 3.

7. The anticoagulant polypeptide of claim 2, wherein the mutant polypeptide is SEQ ID NO: 4.

8. The anticoagulant polypeptide of claim 2, wherein the mutant polypeptide is SEQ ID NO: 5.

9. The anticoagulant polypeptide of claim 2, wherein the mutant polypeptide is SEQ ID NO: 6.

10. The anticoagulant polypeptide of claim 2, wherein the mutant polypeptide is SEQ ID NO: 8.

11. The anticoagulant polypeptide of claim 2, wherein the mutant polypeptide is SEQ ID NO: 9.

12. The anticoagulant polypeptide of claim 2, wherein the mutant polypeptide is SEQ ID NO: 10.

* * * * *

SEQUENCE LISTING

```
<160> NUMBER OF SEQ ID NOS: 10

<210> SEQ ID NO 1
<211> LENGTH: 70
<212> TYPE: PRT
<213> ORGANISM: Artificial Sequence
<220> FEATURE:
<223> OTHER INFORMATION: Sequence derived from Ancylostoma caninum or
      Synthetic

<400> SEQUENCE: 1

Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
    50                  55                  60

Glu Asp Cys Glu Leu Asp
65                  70

<210> SEQ ID NO 2
<211> LENGTH: 71
<212> TYPE: PRT
<213> ORGANISM: Artificial Sequence
<220> FEATURE:
<223> OTHER INFORMATION: Sequence derived from Ancylostoma caninum or
      Synthetic

<400> SEQUENCE: 2

Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
    50                  55                  60

Glu Asp Cys Glu Leu Asp Asn
65                  70

<210> SEQ ID NO 3
<211> LENGTH: 72
<212> TYPE: PRT
<213> ORGANISM: Artificial Sequence
<220> FEATURE:
```

<223> OTHER INFORMATION: Sequence derived from Ancylostoma caninum or
      Synthetic

<400> SEQUENCE: 3

Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
    50                  55                  60

Glu Asp Cys Glu Leu Asp Asn Met
65                  70

<210> SEQ ID NO 4
<211> LENGTH: 73
<212> TYPE: PRT
<213> ORGANISM: Artificial Sequence
<220> FEATURE:
<223> OTHER INFORMATION: Sequence derived from Ancylostoma caninum or
      Synthetic

<400> SEQUENCE: 4

Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
    50                  55                  60

Glu Asp Cys Glu Leu Asp Asn Met Glu
65                  70

<210> SEQ ID NO 5
<211> LENGTH: 69
<212> TYPE: PRT
<213> ORGANISM: Artificial Sequence
<220> FEATURE:
<223> OTHER INFORMATION: Sequence derived from Ancylostoma caninum or
      Synthetic

<400> SEQUENCE: 5

Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
    50                  55                  60

Glu Asp Cys Glu Leu
65

<210> SEQ ID NO 6
<211> LENGTH: 68
<212> TYPE: PRT
<213> ORGANISM: Artificial Sequence
<220> FEATURE:
<223> OTHER INFORMATION: Sequence derived from Ancylostoma caninum or Synthetic

<400> SEQUENCE: 6

```
Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
    50                  55                  60

Glu Asp Cys Glu
65
```

<210> SEQ ID NO 7
<211> LENGTH: 67
<212> TYPE: PRT
<213> ORGANISM: Artificial Sequence
<220> FEATURE:
<223> OTHER INFORMATION: Sequence derived from Ancylostoma caninum or
      Synthetic

<400> SEQUENCE: 7

```
Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
    50                  55                  60

Glu Asp Cys
65
```

<210> SEQ ID NO 8
<211> LENGTH: 74
<212> TYPE: PRT
<213> ORGANISM: Artificial Sequence
<220> FEATURE:
<223> OTHER INFORMATION: Sequence derived from Ancylostoma caninum or
      Synthetic

<400> SEQUENCE: 8

```
Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
    50                  55                  60

Glu Asp Cys Glu Leu Asp Asn Met Glu Phe
65                  70
```

<210> SEQ ID NO 9
<211> LENGTH: 75
<212> TYPE: PRT
<213> ORGANISM: Artificial Sequence
<220> FEATURE:
<223> OTHER INFORMATION: Sequence derived from Ancylostoma caninum or
      Synthetic

```
<400> SEQUENCE: 9

Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
        50                  55                  60

Glu Asp Cys Glu Leu Asp Asn Met Glu Phe Ile
65                  70                  75

<210> SEQ ID NO 10
<211> LENGTH: 76
<212> TYPE: PRT
<213> ORGANISM: Artificial Sequence
<220> FEATURE:
<223> OTHER INFORMATION: Sequence derived from Ancylostoma caninum or
      Synthetic

<400> SEQUENCE: 10

Asn Pro Ser Cys Gly Glu Asn Glu Arg His Asp Glu Cys Ser Arg Lys
1               5                   10                  15

Glu Cys Asp Pro Lys Cys Lys Tyr Asp Gly Thr Glu Glu Lys Asp Asp
            20                  25                  30

Glu Lys Pro Val Val Cys Leu Thr Arg Val Cys Tyr Gly Asp Cys Ile
        35                  40                  45

Cys Arg Asp Gly Phe Leu Arg Asn Lys Asn Gly Ala Cys Val Lys Ala
        50                  55                  60

Glu Asp Cys Glu Leu Asp Asn Met Glu Phe Ile Tyr
65                  70                  75
```